(12) United States Patent
Mazzeo et al.

(10) Patent No.: US 7,510,687 B2
(45) Date of Patent: Mar. 31, 2009

(54) SIMULTANEOUS DETECTION OF DIFFERENT ANTIBODIES AND ANTIGENS IN CLINICAL ALIMENTARY AND ENVIRONMENTAL SAMPLES

(76) Inventors: Alessandra Mazzeo, C. so Mazzini 101, Campobasso (IT) I-86100; Guido Petracca, Via Saint Ercolano, 34, Perugia (IT) I-06100

( * ) Notice: Subject to any disclaimer, the term of this patent is extended or adjusted under 35 U.S.C. 154(b) by 429 days.

(21) Appl. No.: 10/711,847

(22) Filed: Oct. 8, 2004

(65) Prior Publication Data

US 2006/0078954 A1    Apr. 13, 2006

Related U.S. Application Data

(63) Continuation of application No. PCT/IT03/00218, filed on Apr. 9, 2003.

(51) Int. Cl.
*B01L 3/00* (2006.01)
(52) U.S. Cl. .......................... 422/102; 422/50; 422/61; 422/63; 422/65; 422/99; 422/100; 436/518; 436/528; 436/529; 436/530; 435/283.1; 435/287.2; 435/287.3; 435/288.1; 435/288.3; 435/288.4; 435/288.7
(58) Field of Classification Search ................. 436/518, 436/528, 529, 530; 422/50, 61, 63, 65, 99, 422/100, 102; 435/283.1, 287.2, 287.3, 288.1, 435/288.3, 288.4, 288.7
See application file for complete search history.

(56) References Cited

U.S. PATENT DOCUMENTS

| 4,025,391 | A | * | 5/1977 | Kawashima et al. | ......... 435/180 |
| 4,597,927 | A | | 7/1986 | Zeitler et al. | |
| 4,912,043 | A | * | 3/1990 | Terasawa et al. | ............ 435/145 |
| 5,250,412 | A | | 10/1993 | Giegel | |
| 5,494,830 | A | | 2/1996 | Hubscher | |
| 5,882,595 | A | * | 3/1999 | La Motte | ...................... 422/65 |
| 6,153,375 | A | * | 11/2000 | Kobylecki et al. | ............. 435/4 |
| 2005/0089444 | A1 | * | 4/2005 | Justin et al. | ................... 422/63 |

FOREIGN PATENT DOCUMENTS

| DE | 41 20 139 A1 | 12/1992 |
| EP | 0 781 997 A1 | 7/1997 |

\* cited by examiner

*Primary Examiner*—Long V. Le
*Assistant Examiner*—Melanie J Yu
(74) *Attorney, Agent, or Firm*—Thomas E. Toner; Smith & Hopen, P.A.

(57) ABSTRACT

Method and device to simultaneously detect different antibodies and antigens via immunoenzimatic tests and ELISA (Enzyme Linked ImmunoSorbent Assay) constituted by small absorbent cylinders, on which the immunocomplexes are formed, blocked at a modular distance on a probe; that carries a label to identify the sample under examination.

12 Claims, 8 Drawing Sheets

US 7,510,687 B2

SIMULTANEOUS DETECTION OF DIFFERENT ANTIBODIES AND ANTIGENS IN CLINICAL ALIMENTARY AND ENVIRONMENTAL SAMPLES

CROSS REFERENCE TO RELATED APPLICATION

The present application is a continuation of a prior filed International Application, serial number PCT/IT03/00218, filed Apr. 9, 2003, which International Application claims a priority date of Apr. 11, 2002 based on prior filed Italian patent application serial number No. CZ2002A000002.

SUMMARY OF THE INVENTION

This invention refers to a method to simultaneously detect different antibodies and antigens. Said method is based upon the use of a device which allows the introduction of the solid phase of an immunoenzimatic reaction directly into the sample to be examined, thus inverting the procedure of the first step in the execution of the immunoenzimatic methods and in those of ELISA (Enzyme Linked ImmunoSorbent Assay), which generally foresee that the sample be distributed among the microwells of microplates, on the surface of which the single type (solid phase), reagent, antigen or antibody is adsorbed.

BRIEF DESCRIPTION OF THE FIGURES

In FIG. 1 there are eight of the small cylinders (2) set out on the rod, but they could also be four or twelve.

Figure 1:
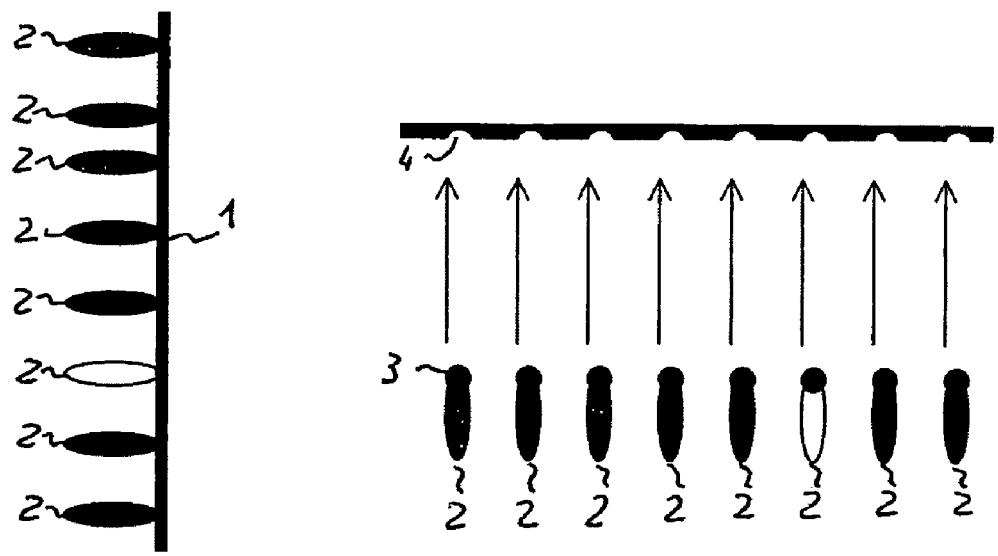
FIG. 1 represents a metal or plastic rod (1), from which protrude the equally distanced small cylinders (2) of solid adsorbent material, such polystyrene or nylon for example. The small cylinders (2) can also be single and in the case they are fixed by means of joints (3) to the notches (4) made in the rod (1). The system of fixing joint (3) to notch (4) allows assembly at will of the small cylinders (2) to the rod (1).

The rod has a label (6) that is detached and inserted into the lid of the sample's container (5b).

The transport time for the sample's container (5) with the rod (1) furnished with small cylinders (2) is used as incubation time for the formation of the immunocomplex on each individual small cylinder (2).

Figure 3:
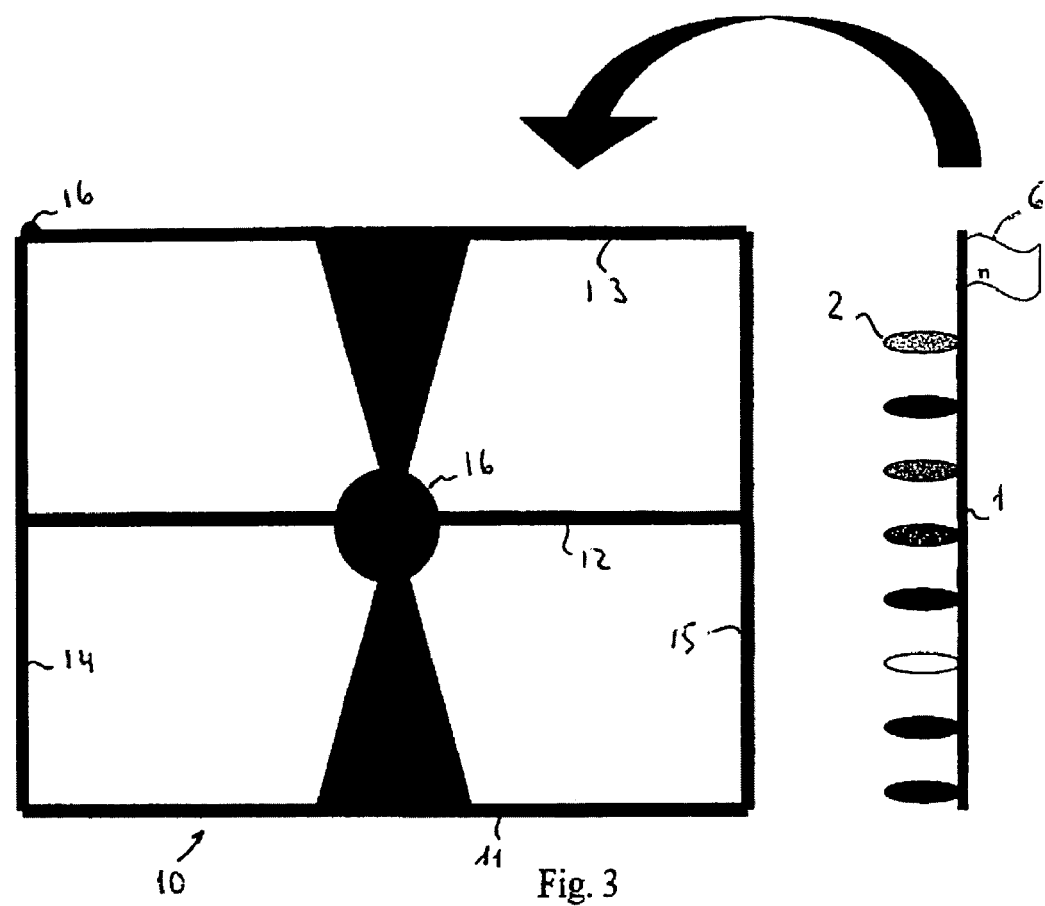

FIG. 3 shows how, at the end of the incubation period, each rod (1) with the small cylinders (2) with labels (6) is placed on a grill (10) formed by at least three parallel horizontal sides (11, 12, and 13) and with at least two parallel vertical sides (14 and 15) and with a handle (16) for lifting and/or transport. For the housing of the rods, twelve notches area available, equally distanced on the horizontal sides (11, 12, and 13) and eight notches equally distanced on the vertical sides (14 and 15).

Figure 4:
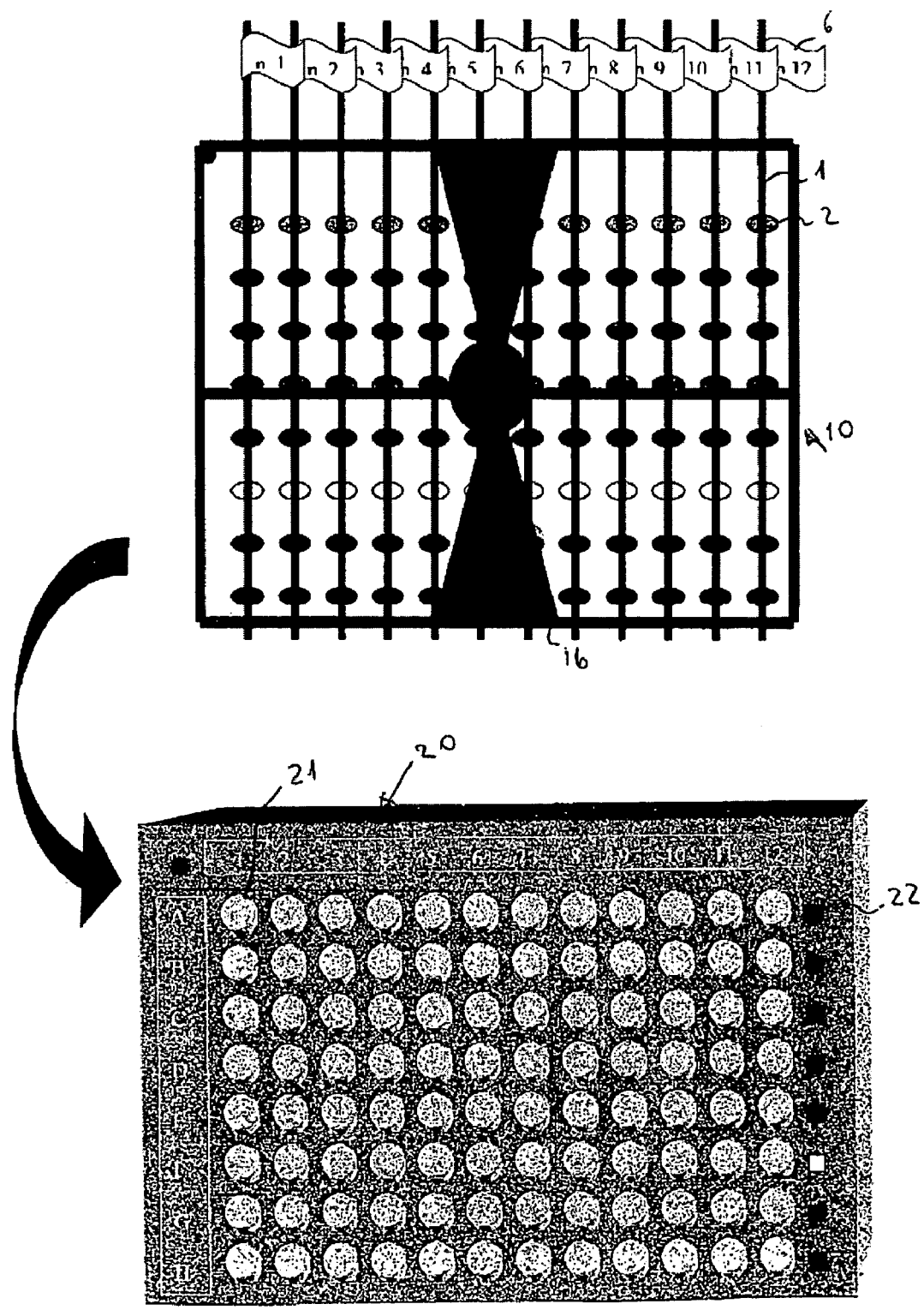

To indicate the direction of loading the rods onto the grill (10) a colored button (16) is displayed on it. On the grill (10) the rods (1) are laid out according to the colored button (16). In FIG. 4 the rods (1) are placed in the notches present on the parallel horizontal sides (11, 12, and 13), and a microplate (20) is shown, that has ninety-six microwells, (21) laid out in twelve columns numbered from 1 to 12 and eight lines indicated from A to H. The lines are also distinguished by differently colored small squares (22).

Figure 5:
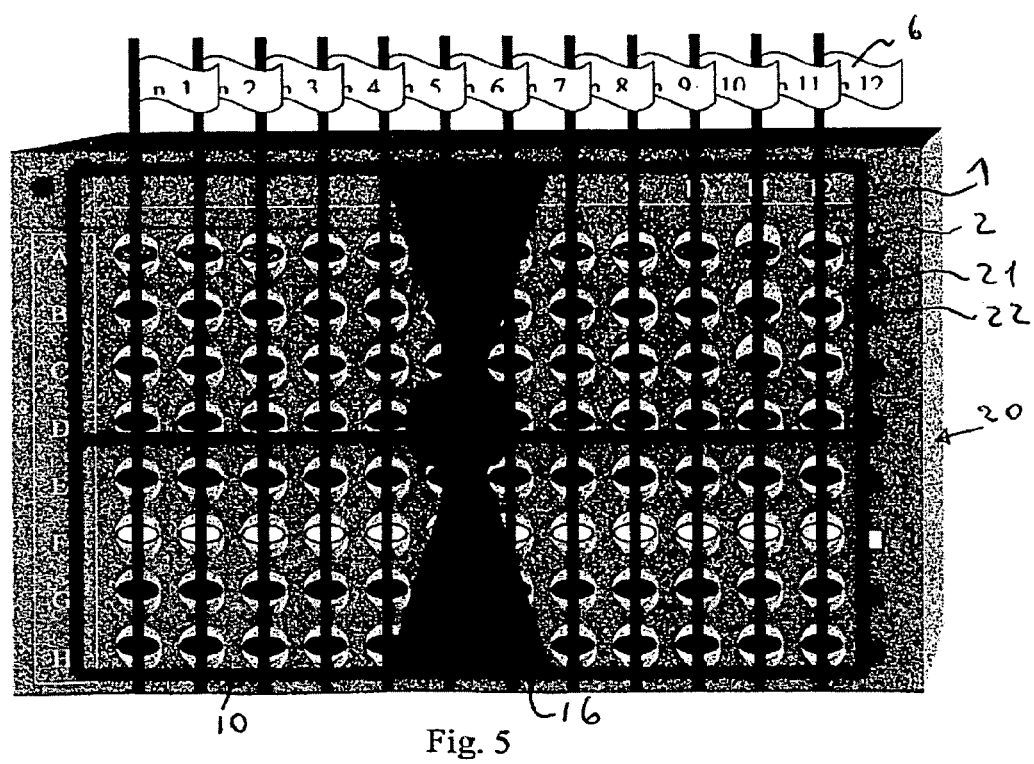

The grill (1) is of a shape and size sufficient to consent the loading of the rods (1) in such a way as to make the position of the small cylinder (2) coincide with that of the same microwells (21) disposed on the microplate (20), as illustrated in FIG. 5.

Figure 6:
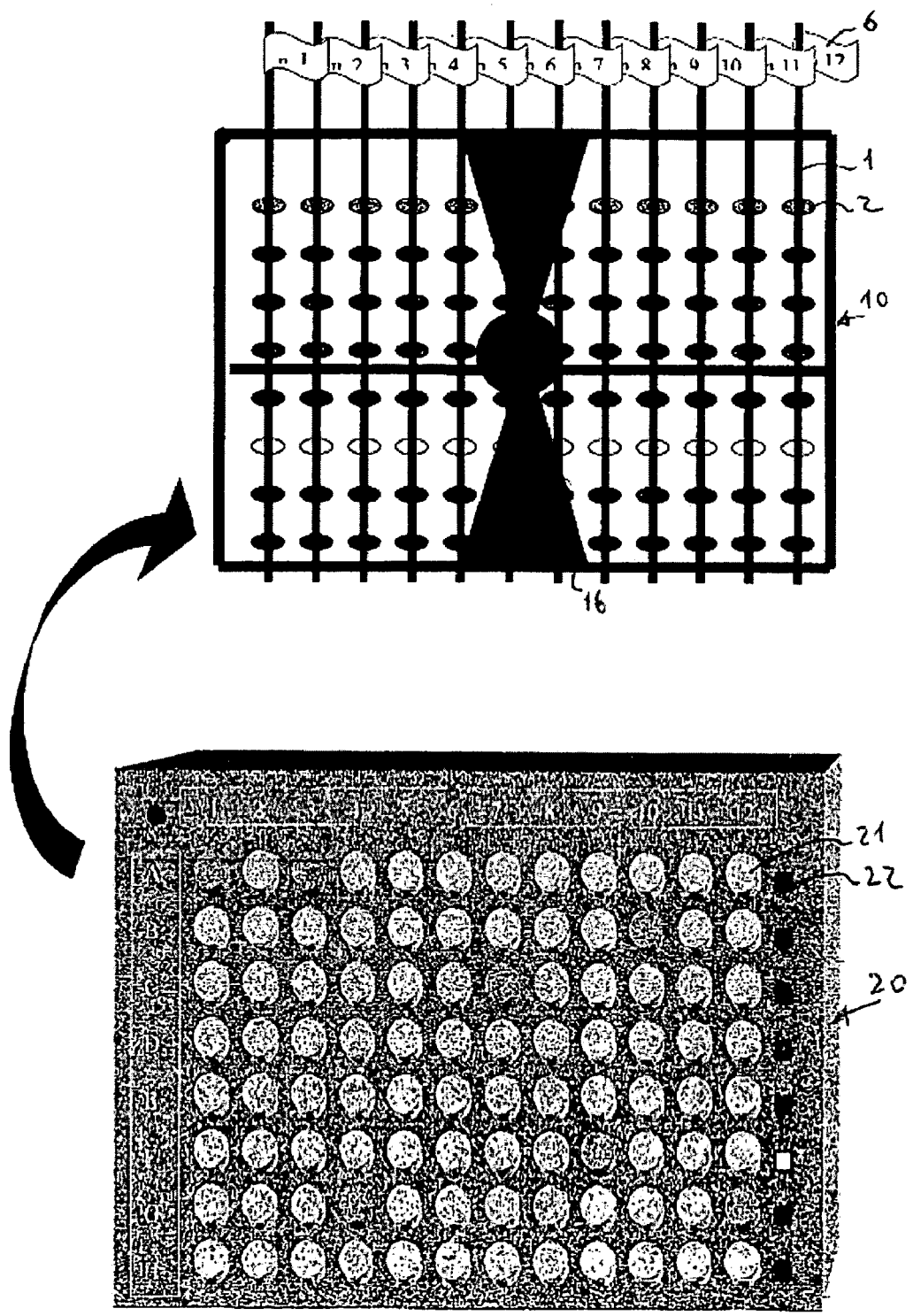

FIG. 6 shows the grill (10) that is lifted from the microplate (20) for cleaning.

Figure 7:
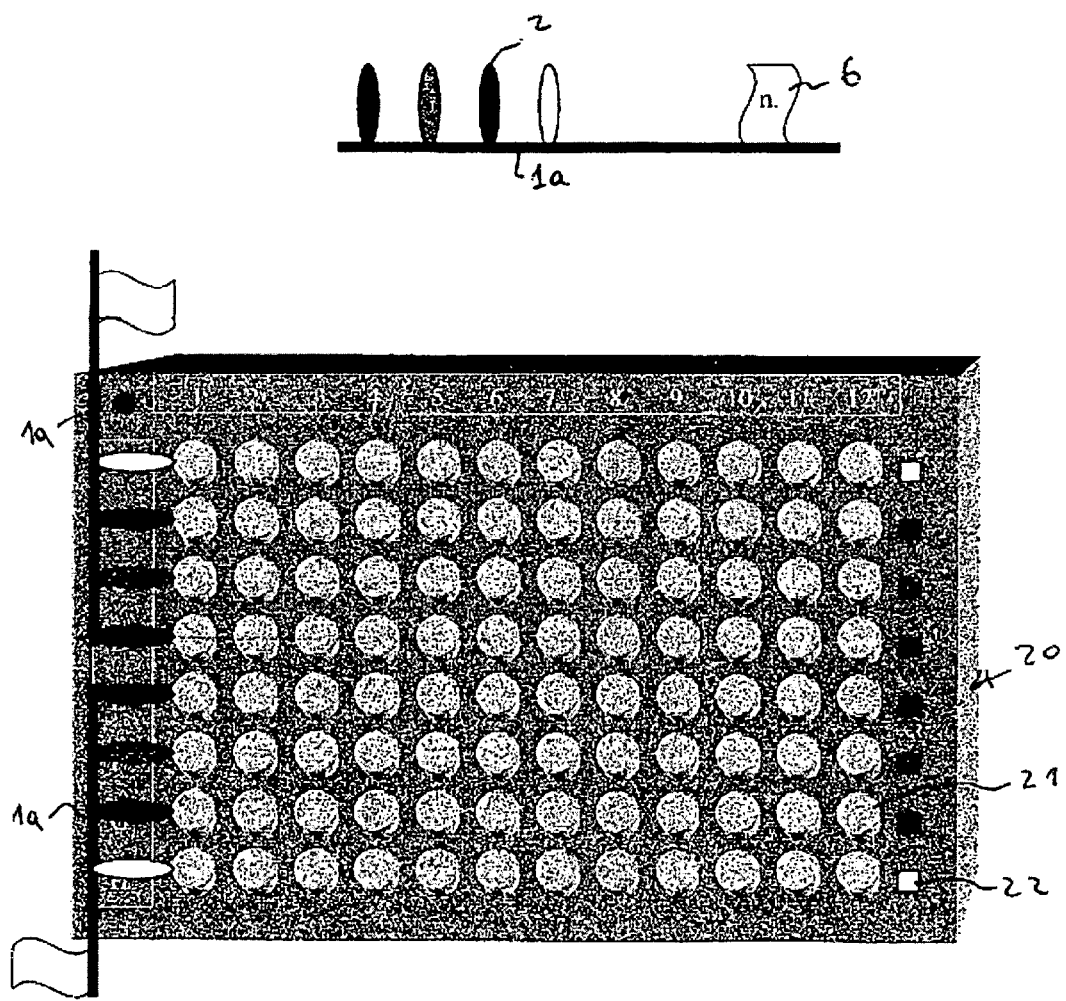

In FIG. 7 a rod (1a) is shown, with four small cylinders (2) and with a label (6). The rod (1a) in the same figure is laid on the twelve columns of the microplate (20) from one side to the other, doubling the microplates capacity to carry out analyses on double the number of samples. Consequently the small colored squares (22) that will be symmetrically repeated are modified on the microplate.

Figure 8:
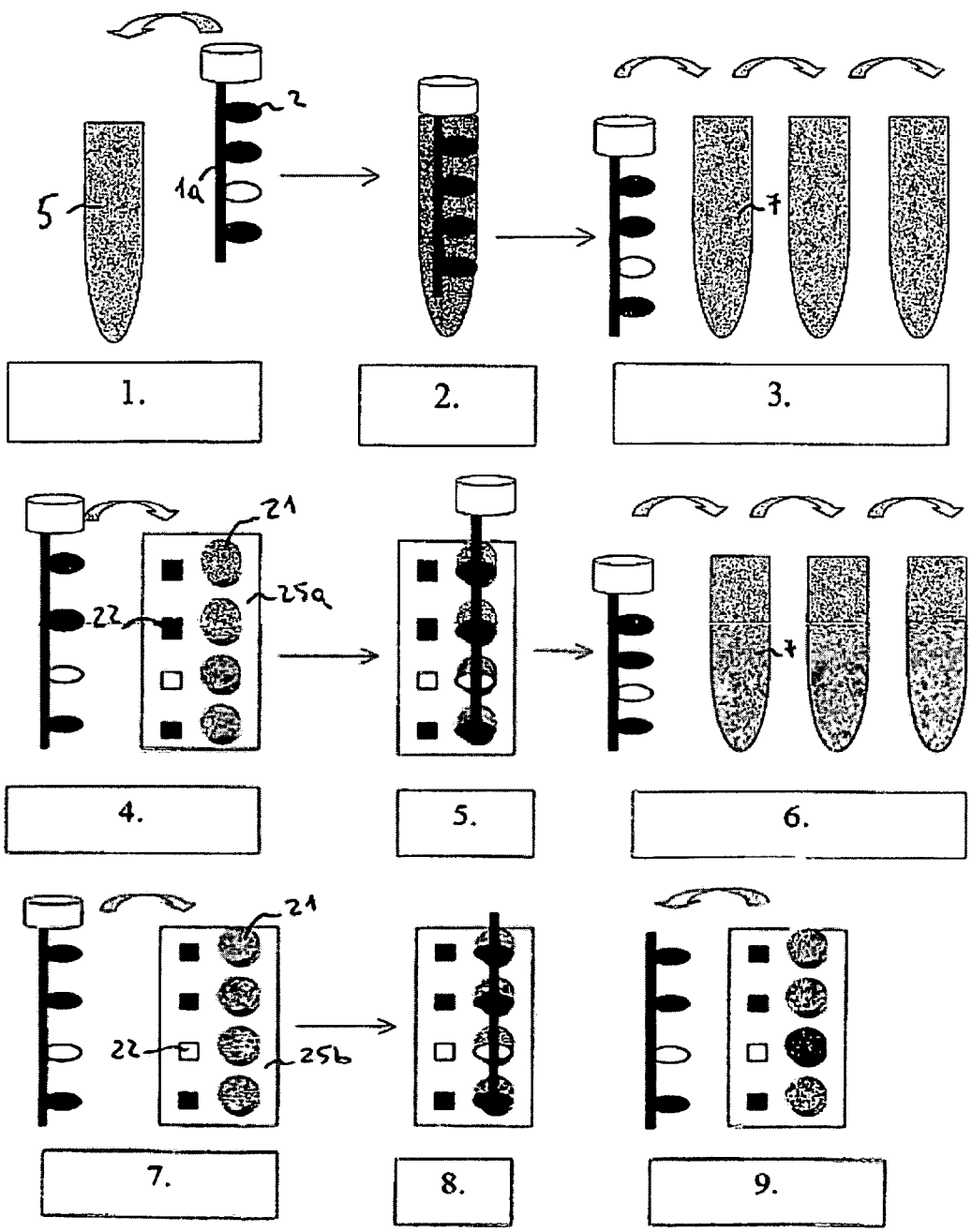

Summarizing the procedure, as shown in FIG. 8, a series of adsorbent cylinders 2 attached to rod 1a are inserted into a sample tube 5 with a collected sample. After incubation, the cylinders are washed, as shown in FIG. 8(3) and probed as shown in FIGS. 8(4) to 8(9).

DETAILED DESCRIPTION OF THE PREFERRED EMBODIMENT

In the proposed method the solid phase carries diverse adsorbed reagents (antigens and antibodies) for various simultaneous analyses and is represented by the surfaces of small protruding cylinders from a rod, which is introduced directly into the sample and later, after incubation, placed on a screen for microplates or microstrips, which is moved from the microwells of a first microplate, which contains the conjugate, to a microplate (or microstrip) where the chomogenous sub layer is distributed. This last, once removed from the screen that holds the small cylinders, then passes through a spectrophotometer for a reading: this allows the use of equipment that is already on sale and is normally used in laboratories for analysis and dose not constitute, therefore, an economic obstacle to the wider distribution of the innovation.

The small cylinders can be single and assembled on the probes, according to the analytical necessities, or those of research, or the can be set out in numbers of 4 or 8 or 12 for each rod, according to specific panels that respond to the principal diagnostic exigencies (FIG. 1).

The versatility of the proposed invention makes the method of various types of approach, both experimental and routine, extremely flexible and adaptable, and permits the slimming down and optimization of laboratory fields that foresee the use of immunoenzimatic tests and ELISA.

State of the Art

The methods and the device used up to the present date for the detecting of antibodies and antigens, that foresee the use of immunoenzimatic tests and ELISA, present some very delicate steps that condition the analytic result and which need particular care. There are:

Cleaning the solid phase, constituted of microwells of small dimension;

Drying the same solid phase;

The different times of contact of the reagents that are manually distributed in the microwells, with the consequent possibility of systematic errors.

Furthermore, these tests are conditioned by:

Processing times for the samples that suffer in the time necessary for the distribution of the various samples among the microplates and for the transcription of the identifying codes;

The volume of samples on which to execute the analysis, which limits the sensitivity of the test, and which cannot be varied because it depends on the number of the microwells of the microplates;

The necessity to execute the various analyses for a single sample in different microplates.

To overcome these inconveniences, several solutions have been proposed, among them those described in the following patent documents: DE 4120139, EP-A1-0301141, EP-A-0087899.

In DE 4120139 microwells are made on a microplate, arranged in diverse parallel lines and columns. A secondary cover for the microplate creates a structural support that binds the antigen or antibody, also disposed along lines and columns corresponding to the geometry of the microwells, so that by covering the microplate with the supporting cover they penetrate perfectly into the microwells. In each dimple of the individual microplates a sample to be analyzed is placed by pipette. The cover that holds the supporting structure for the antigen again covers the microplate, and it is allowed to incubate for sufficient time to allow the formation of the immunocomplex. Once formed, the immunocomplex remains stuck to the distal part (the beads) of the support. The first cleaning of the supports occurs inside the microwells. The entire cover, together with the supporting structures for the antigen, is transferred onto another microplate, in which the conjugate antispecies has been distributed, and it is left to incubate once again. If the immunocomplex is present, it will bind to it. A second cleaning is performed. The cover is once again transferred onto a third microplate, in which the chromogenous sub layer has been distributed. Finally, it is put aside to incubate to permit the chromogenous action to happen.

The samples to be analysed must be quickly deposited singularly onto the first microplate.

In EP-A1-0301141, a variety of specific antibodies for different antigens can be simultaneously determined in a single clinical sample.

The invention comprises:
A support structure that is preferably plastic, provided with a group of openings ellipsoidal in shape;
A porous membrane of immobilised nitrocellulose on said support, on which the different antigens are sprayed;
Binders (double adhesive layers) to immobilize said membrane on the supporting member;
A first container, containing the diluted sample of serum/whey to be analysed;
A second container containing the conjugated antispecies;
A third container that contains the chromogenous sub layer.

The sustaining member, on the membrane of which the different antigens are adsorbed, is inserted into the first container that holds the sample to be analyzed. It is allowed to incubate for five minutes, during which time the formation of the immunocomplex that remains adhered to the membrane takes place. There follows a phase of cleaning the support member with distilled water, to eliminate the non bound residues, and later the support is inserted into a second container in which the conjugate alkalin-phosphatase antispecies has been distributed. There then follows an ulterior incubation, during which the conjugate binds to the immunocomplex (said aggregate, a conjugate-immunocomplex, will always remain adhered to the support). The third cleaning then takes place. In the final phase the supporting structure is inserted into a third container that contains the chromogenous substrate. The alkaline phosphatase (an enzyme of the conjugate) convets the soluble chromogenous sub layer into an insoluble colored product that is deposed onto the porous membrane. The products so bound are visible in the form of colored marks on the porous membrane. The absence of the colored markings on the membrane indicates the absence of specific antibodies in the clinical sample.

In EP-A-008799, microwells disposed in a number of parallel columns and lines are laid out on a microplate. A secondary cover over the microplate presents supporting structures that constitute the solid phase for anchoring the immunocomplex that are removable, though connected by a breakable appendix these too, are laid along lines and columns that correspond to the geometry of the microwells, in such a way that when the microplate is covered with the cover then the support structures penetrate perfectly into the microwells. In each dimple the sample to be analyzed is distributed. The microplate is covered again with the cover that sustains the support structures for the antigen and it is allowed to incubate for sufficient time to permit the formation of the immunocomplex. Then follow the phases of the ELISA methodology.

Some of the methods analyzed do no resolve the problem of the distribution of the samples among microplates and the transcription of the identification codes, with a notable loss of time and with the possibility of error, while others do not consent the execution of the analyses for the search for antigens in the samples.

Another disadvantage is represented by the fact that the incubation time starts only from the moment when the microwells in the microplates have been filled.

To overcome these inconveniences and disadvantages, and to optimize the analytical procedure, the present device and method for simultaneous detecting of different antibodies and antigens is proposed, which, by way of example but not limited to, is used for:
A)—the simultaneous search for different antibodies in:
Mass samples of milk;
Individual blood samples (animal or human) with an anticoagulant;
Samples of saliva
Egg samples;
B)—the simultaneous search for different antigens (microorganisms of interest in the medical or veterinary fields or their toxins, xenobiotic substances etc.) in:
Pathology samples;
Food samples;
Environmental samples
C)—the simultaneous search for different antibodies and different antigens in:
Mass samples of milk;
Individual samples of blood (animal or human) with an anticoagulant;
Saliva samples;
Egg samples;
Pathology samples The sensitization of the solid phase
solid phase is constituted by the surfaces of the small cylinders of plastic material that are suitable for use in immunoenzimatics (polystyrene, nylon, acrilonitric styrne etc.) end is sensitized using the current methods which foresee the contact of the surface to be sensitized with the protein reagent (antibody or antigen) in a tampon of carbonate/bicarbonate of pH=9:5 and incubation for a night at refrigerator temperature.

The substantial difference between this sensitizing procedure in respect to the classic method consists in the fact that the containers utilized for sensitizing the small cylinders are filled with different reagents (whilst in the classic method all the microwells of a microplate are sensitized with the same reagent) in such a way that each small cylinder from the same probe brings diverse adsorbed reagents to the surface. For example, if one uses a microplate with 96 small microwells for the sensitization of the small cylinders carried by 12 rods, each with 8 small cylinders, then the microplate would be charged in the following manner:

Line A: reagent A in all 12 microwells
Line B: reagent B in all 12 microwells
Line C: reagent C in all 12 microwells
Line D: reagent D in all 12 microwells
Line E: reagent E in all 12 microwells
Line F: reagent F in all 12 microwells
Line G: reagent G in all 12 microwells
Line H: reagent H in all 12 microwells In this way, at the end of the procedure for the sensitizing of the solid phase, each of the 12 rods with 8 small cylinders is useful for carrying out 7 different tests plus a negative control contemporarily, and each rod will have an identical sequence.

The solid phase prepared in this way is conserved in a refrigerator until the moment of analysis.

The Analysis Samples

Figure 2:
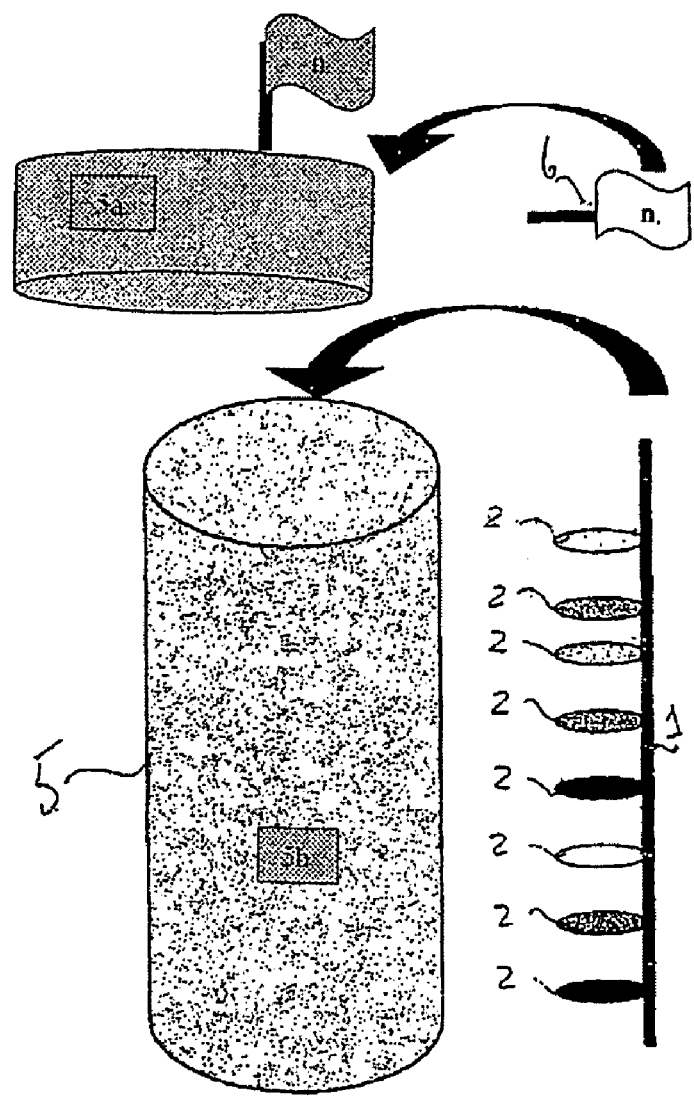
FIG. 2 shows a rod (1), where the small cylinders (2) have all been previously sensitized with a different protein reagent (antibody or antigen), which is immersed into the container (5a) for the sample for the search for antigens and antibodies.

The sample (for example blood with an anticoagulant, or milk) is collected in bottles or test-tubes (in which is placed an equal quantity of diluting liquid) into which a rod is immerged—in a specific predisposed lodging on the inside of the lid cover that then closes the sample's container—bringing the small cylinder where the antigens are adsorbed towards the sample to be examined for antibodies (and/or to ascertain the presence of antibodies directed towards antigens): each small cylinder holds a different antigen (or a different monoclonal antibody) and can be distinguished by a particular coloring (FIG. 2); one small cylinder is not sensitized with any antigen and acts as a negative control (the probes can be assembled in such a way as to contain—an antigen plys the negative control;—up to 7 antigens plus the negative control, as shown in the illustration;—up to 11 antigens plus the negative control, inverting the direction of the microplates and using rods with 12 small cylinders).

The cover or lid for the samples' containers is also furnished, on the outside with a specific holder for the card bearing the sample's identification code; said card is placed on the cover at the moment the sample is taken and, at the time of the sample's processing, is taken from the cover and put onto the rod. The time involved in the laboratory for transporting the samples is used as a period of incubation for the formation of immunocomplex, if there should be specific antibodies present in the sample when they confront the adsorbed antigens in the small cylinders (and/or the specific antigens for the monoclonal antibodies adsorbed in the small cylinders).

Should the sample prove positive for one or more antigens (or antibodies) present on the rod that has been inserted, the immunocomplex that forms adheres to the surface of the respective small cylinder by the specific antigen (or antibody); in fact, the reaction makes use of the adsorbment of the antigent (or antibodies) at the solid phase, represented by the small cylinders. This solid phase that detens the immunocomplex goes through further steps. On arrival at the laboratory, the container holding the sample is opened, the rod bearing the small cylinder is removed, and provided with its own card bearing the identification code for the sample, then placed, together with the other rods from different samples, on a specific holder in the form of a grill for microplates (FIG. 3); in the case of a single sample it will be placed on a support for microstrips.

A thorough cleaning takes place, bathing the small cylinders with a special solution and the cleaning liquid is left to drip dry, placing the extremity of the small cylinder onto blotting paper (it is sufficient to place it onto the paper). In this manner any traces of matter adhering to the surface of the small cylinders is removed, since it is not specifically bound to them, while the antibodies (or the antigens) working in the formation of the immunocomplex remain adhered to the specific antigens (or antibodies) adsorbed by the small cylinders surface.

The conjugate anti-species is dispensed among the microwells of a microplate or microstrip that has not adsorbed any kind of reagent, and is immediately covered by the holder bearing the rods, in such a way that the small cylinders dip into the reagent and the color of the small cylinders corresponds to a colored strip born on the side of the microplate or the microstrip holder (FIG. 4, FIG. 5), should one want to use holders marked by color (in the case of the search for the antigens in the sample under examination, the conjugate will be constituted of an enzyme bound to a monoclonal or polyclonal antibody directed at an epitope of the antigen that is different to the one that binds to the monoclonal antibody adsorbed onto the small cylinders' surfaces). It is left to incubate (generally 30' at +37° C.).

During the incubation period the conjugate, that is the antibody bound to an enzymatic protein capable of catalyzing the chromogenic reaction in the presence of the specific sub layer, binds specifically to the immunocomplex whenever this has been formed during the preceding incubatory phase with the rod inserted in the sample to be examined. Should the sample be positive then the conjugate will also remain adhered to the surface of the small cylinders and will be transported with them in the final microplate.

After incubation the holder bearing the rods is taken away and a further cleaning and drying takes place, to eliminate the reagents that do not adhere specifically to the small cylinders' surfaces, while the antigen/antibody/conjugate complex (or that of the antibody/antigen/conjugate complex) remains firmly adhered.

The holder bearing the rods is placed onto another, final, microplate or microstrip, where the chromogenous sub layer has been dispensed.

It is left to incubate (generally 10-15 minutes at room temperature), to allow catalysed reaction of the enzyme bound to the conjugate that brings to the development of a colored substance (chromogenous reaction) to take place, the quantity of which is proportional to the quantity of the immunocomplex that adheres to the small cylinders and the optical density of which is measurable by spectrophotometer. The chromogenous reaction is simply blocked by lifting the supports; that is, by extracting the small cylinders that hold the conjugate adsorbed with the enzyme (FIG. 6).

A spectrophotometer reading of the microplate or microstrip is taken. The same procedure is followed for the probes with 4 or 6 or 12 small cylinders (FIG. 7).

Should one want to carry out the method exclusively in a laboratory, omitting to insert the rod bearing the small cylinders directly into the sample and collection container to be analyzed, one can proceed to the distribution of the samples into the microwells (into which an opportune quantity of diluting liquid can eventually be placed) of a microplate that has not been sensitized by any reagent, by using a micropipette. In this case as many replicates of the sample must be distributed as there are small cylinders for the rods that will successively be inserted into the microwells containing the sample, and the same direction of placing the rods inserted into the frill must be observed (for example, in the case of 8 small cylinder rod, in a microplate 12 samples are distributed, each one replicated 8 times, that is in the 8 microwells that form a column). Once the distribution of the samples among the microplates has taken place, the grill containing the rods bearing the small cylinders is placed, in such a way that they dip into the samples to be analyzed and it is left to incubate at a suitable temperature for the necessary time. At the end of the incubatory period one proceeds to the cleaning of the small cylinders, and immerges them into the microwells of the microplate that contain the specific conjugates and they are allowed to incubate at a suitable temperature for the necessary time. One then proceeds to a further phase of cleaning the small cylinders and their immersion into the microwells of the microplate that contain the chromogenous sub layer; they are left to incubate for the necessary time at a suitable temperature, the grill containing the probes with the small cylinders is lifted, and one proceeds to take a spectrophotometer reading.

Advantages and Merits of the Methods of This Invention

The execution time for this type of test in a laboratory is about 50 minutes in total, while the classic method takes decidedly longer, thanks to the necessity of transferring a proportional amount of the sample onto the microplate, transcribe the identification codes for the samples in the order of their distribution on the microplate, allowing the samples to incubate with the adsorbed antigen at the solid phase constituted by the walls of the microwells of the microplate, everything to be multiplied by a number of times equal to the number of tests to be carried out for the same sample.

Two cleanings occur, as with the classic method.

The incubatory periods, following the addition of the conjugate and after the addition of the chromogenous sub layer, ware equal to those of the classic method.

An extra microplate is necessary with respect to the classic method, non-sensitized by any type of reagent and therefore of very low cost.

The cost of the rods bearing the small cylinders onto which the antigens (our antibodies) are adsorbed is comparable to that of the microplates sensitized with antigens or antibodies.

The cost of the holders for the rods bearing the small cylinders should only be considered an initial cost, such as a cost for laboratory material (just as for test-tubes racks).

Merits of the Method

The advantages offered by the proposed invention are distinguished in general advantages—that is, in the improvements to the quality of the classic immunoenzimatic method—and in advantages of a specific kind; that is, relative to specific applications in the field of health.

General Advantages

The optimization of the cleaning procedures during the solid phase derives from the possibility of investing the small cylinders with a flow of cleaning solution far more efficient in the removal of non-specific reagents capable of altering the reaction;

The optimization of the drying procedures during the solid phase and consequently the conformity of the small cylinders, that allows the liquid in which they had been previously immersed to drip easily;

The reduction of systematic errors deriving from the contact of each sample of the microplate with the reagents at the same time;

The reduction in the processing times for the sample is made possible by using the transport time to the laboratory as a first-step period of incubation;

The reduction in the processing times for the sample is, furthermore, tied to the abolition of one step in the procedure, given that the solid phase, to which the conjugate is eventually anchored, is extracted from the final microplate, making the inoculation of the solution that blocks the chromogenous enzymatic reaction unnecessary;

An improvement to the test's sensitivity derives from the possibility of increasing the quantity of the sample to be analyzed according to will, without increasing the quantities of reagents necessary to carry out the test; the quantity of the sample under exam is separated, therefore, from the quantity of the reaction, and this brings about an increase in the sensitivity of the test, above all in mass milk samples, in food samples, and in environmental samples (in the case of food and environmental samples, the possibility of predisposing monoclonal antibodies capable of reacting with the un-denatured bacterial antigens should be studied; this would make it possible to use the proposed method in a greater quantity of samples compared to that used in the classic immunoenzimatic method, thus avoiding the need to fall back on the enriching phase—the release of the analytical report 24 hours prior to that of the classical method—or to eliminate the phases of pre-enrichment and enrichment, with the release of the analytical report 48 hours ahead of the classical method; it remains to be carefully evaluated, however, the significance to be attributed to the positive reactions that are not preceded by a phase of growth of bacteria).

Specific Advantages:

The possibility of processing battery samples, that is at the same time for the entire range of tests to be carried out (breathing panel, enteric panel, panel of animal health during weaning, pathogens and toxins in foodstuffs etc.) responds in a congruous manner to the needs of diagnostic serology and of food and environmental control, that rarely foresee on single type of test per sample, allowing the release of the complete analytical report at the end of one single test.

The solid phase, constituted by the small cylinders, can be planned to allow the assembly of the individual small cylinders at any time, according to the diagnostic needs that occur on each occasion.

Precautions

In the case of carrying out mixed tests in the search for different antigens in the same sample, together with a search for different antibodies or not, it should be noted that while the same conjugate anti-species can be used in the search for any type of antibody, in the search for the antigens a specific conjugate is used for each type of antigen; in the first microplate used in the laboratory on the arrival of the sample, a specific conjugate is placed on each line or column to show up specific antigens; to make this distribution easier, the bottom of the microwells of the microplate can be colored, give that this microplate does not go through a spectrophotometer reading.

Other characteristics and advantages of the invention will appear clear from the following description of several methods for constructing the invention, given only an non-limiting examples in the FIGS. 1,2,3,4,5,6,7 and 8.

As illustrated in FIG. 8, the method lends itself to the creation of kits for the examination of samples in the field or in laboratories (medical or veterinary), thanks to the simplification of the procedures for the distribution of the sample, the cleaning at the solid phase, and to the possibility to carry out simultaneously the detection of more antibodies and/or antigens. In this case the spectrophotometer reading can be substituted by a visible reading of the results of the test.

FIG. 8 represents the steps to carry out for an analysis of a single rod (1a) with four small cylinders (2).

Step 1. Taking the sample and introducing the rod into the container (5) (eventually graduated and already containing the dilution solution).

Step 2. Incubation at room temperature.

Step 3. Three passages in test-tubes (7) containing the cleaning liquid.

Step 4. The introduction into a microstrip (25a) that already contains the specific conjugates.

Step 5. Incubation at room temperature.

Step 6. Three passages in test-tubes (7) containing the cleaning liquid.

Step 7. The introduction into a microstrip (25b) that already contains the chromogenous sub layer.

Step 8. Incubation at room temperature.

Step 9. The visible reading of the results.

On each microplate (25a) or (25b) made from a single column of microwells, that is a microstrip, the antibodies or antigens to be sought are indicated by specific small colored squares (22)—for example, antigen A, antigen B, monoclonal antibody, no reagent (negative control)—the color of which corresponds to that of the small cylinders (2).

The Preparation of Positive Controls

For each microplate or series of microplates or microstrips, the positive control is prepared by previously placing a rod in incubation—the small cylinders of this rod are immersed in microwells that contain the specific reagents for the positive control of the test (antigens and antibodies)—for the necessary period and at a suitable temperature (the small cylinder that ahs not been sensitized by any reagent is inserted into a dimple without any specific reagent and serves as an ulterior negative control); the rods on which the immunocomplex has formed can eventually be conserved, ready for use. The positive control rod is then inserted into the grill in which the rods extracted from the samples are loaded, and is examined at the same time as these rods, and with them follows the above described test procedures. The invention, it must be noted, is not limited in use to the examples give in the illustrations, but can be modified and perfected by anyone skilled in the art without breaking patent.

What is claimed is:

1. An assay device for simultaneously detecting different antibodies and antigens via immunoenzimatic tests and ELISA—Enzyme Linked ImmunoSorbent Assay comprising:

adsorbent cylinders on which immunocomplexes form;

a rod bearing the adsorbent cylinders at positions which protrude a modular distance from the rod, wherein the rod bearing the cylinders thereon is able to be inserted into a test tube containing a sample so that the sample can be directly introduced to the cylinders;

a label positioned on the rod to identify the sample collected in the test tube;

a support for carrying a plurality of the rods bearing the cylinders;

a microplate having a plurality of wells filled with an ELISA reagent, wherein the wells are positioned at the modular distances and the positions of the adsorbent cylinders on the rods penetrate into the wells when the support is positioned above the microplate.

2. The device according to claim 1 wherein the support is a grill formed of at least two parallel horizontal sides and of at least two vertical parallel sides, said grill has a handle for transport and lifting, and a plurality of notches on the horizontal and vertical sides for situating the rods.

3. The device according to claim 2 wherein the grill supports twelve rods, and each of the rods bears eight adsorbent cylinders, and the microplate comprises ninety-six wells positioned in an array of twelve columns by eight lines at the modular distances.

4. The device according to claim 2 wherein the grill supports eight rods and each of the rods bears twelve adsorbent cylinders, the grill is positioned above the microplate, and the microplate comprises ninety-six wells arranged in twelve columns and eight lines at the modular distances.

5. The device according to claim 2, wherein the grill supports twenty four rods each of the rods bearing four cylinders, the rods are arranged on the grill and the grill is positioned above the microplate, wherein the microplate comprises ninety-six wells arranged in twelve columns and eight lines at the modular distances.

6. The device according to claim 2, wherein the grill supports sixteen rods arranged on the grill, and the grill is positioned above the microplate, wherein the microplate comprises ninety-six wells arranged in twelve columns and eight lines at the modular distances.

7. The device according to claim 1, wherein the microplate is a microstrip comprising twelve wells.

8. The device according to claim 1, wherein the rod bearing the small cylinders comprises a place to position a card bearing the identification code of the sample, wherein the card can be removed and inserted into a specific holder on the cover or lid for the test tube comprising a sample and the cover or lid also comprises an external site for the card.

9. The device according to claims 1 and 7, wherein the rods, adsorbent cylinders, test tubes, and microstrip are constructed entirely for the carrying out the test in the field or in non-specialist surgeries or laboratories.

10. The device according to claim 1, wherein each adsorbent cylinder of the device is sensitized with a different antigen for antibody detection assay or with a different antibody for antigen detection assay, with the exception of one adsorbent cylinder that is not sensitized.

11. The device according to claim 1, wherein each adsorbent cylinder of the device is sensitized with a different antibody for antigen detection assay, with the exception of one adsorbent cylinder that is not sensitized.

12. The device according to claim 2 wherein the grill supports a plurality of rods, and each of the rods bears a plurality of adsorbent cylinders, and the microplate comprises a plurality of wells positioned at the modular distances.

* * * * *